United States Patent
Hakamada et al.

(10) Patent No.: US 7,364,891 B2
(45) Date of Patent: Apr. 29, 2008

(54) MUTATED ALKALINE CELLULASE

(75) Inventors: Yoshihiro Hakamada, Tochigi (JP);
Tadahiro Ozawa, Tochigi (JP); Tooru Kobayashi, Tochigi (JP)

(73) Assignee: Kao Corporation, Tokyo (JP)

( * ) Notice: Subject to any disclaimer, the term of this patent is extended or adjusted under 35 U.S.C. 154(b) by 107 days.

(21) Appl. No.: 10/510,716

(22) PCT Filed: Apr. 25, 2003

(86) PCT No.: PCT/JP03/05371

§ 371 (c)(1),
(2), (4) Date: Oct. 18, 2004

(87) PCT Pub. No.: WO03/091422

PCT Pub. Date: Nov. 6, 2003

(65) Prior Publication Data

US 2005/0287656 A1    Dec. 29, 2005

(30) Foreign Application Priority Data

Apr. 25, 2002   (JP) .................. 2002-124474

(51) Int. Cl.
*C12N 9/42*    (2006.01)
*C12N 1/12*    (2006.01)
*C12N 15/74*   (2006.01)
*C12P 21/06*   (2006.01)
*C12P 19/34*   (2006.01)
*C07H 21/04*   (2006.01)

(52) U.S. Cl. .................. 435/209; 435/69.1; 435/91.1; 435/252.3; 435/320.1; 435/471; 536/23.2

(58) Field of Classification Search ............... 435/183, 435/320.1, 252.3
See application file for complete search history.

(56) References Cited

FOREIGN PATENT DOCUMENTS

EP   0 269 977 A2   6/1988
JP   2001231569 A  *  8/2001

OTHER PUBLICATIONS

Sumitomo et al., Nucleotide sequence of the gene for an alkaline endoglucanase from an alkalophilic *Bacillus* and its expression in *Escherichia coli* and *Bacillus subtilis*. Biosci. Biotech. Biochem., 1992 vol. 56 (6): 872-877.*

Whisstock et al., Prediction of protein function from protein sequence and structure. Q. Rev. Biophysics., 2003. vol. 36 (3): 307-340.*

Jae-Seon Park, et al., "Identification of two amino acids contributing the high enzyme activity in the alkaline pH range of an alkaline endoglucanase from a *Bacillus* sp.", Protein Engineering, vol. 6, No. 8, XP-009048909, 1993, pp. 921-926.

Katsuya Ozaki, et al., "Molecular cloning and nucleotide sequence of a gene for alkaline cellulase from *Bacillus* sp. KSM-635", Journal of General Microbiology, vol. 136, XP-002225733, Jul. 1990, pp. 1327-1334.

Endo, K. et al., A novel alkaline endoglucanase from an alkaliphilic *Bacillus* isolate: enzymatic properieties, and nucletide and deduced amino acid sequences., Appl. Microbiol. Biotechnol., 2001, vol. 57, Nos. 1 to 2, pp. 109 to 116.

* cited by examiner

*Primary Examiner*—Rebecca E Prouty
*Assistant Examiner*—Ganapathirama Raghu
(74) *Attorney, Agent, or Firm*—Oblon, Spivak, McClelland, Maier & Neustadt, P.C.

(57) ABSTRACT

A mutated alkaline cellulase derived from a cellulase having the amino acid sequence represented by SEQ ID NO: 1 or one having a homology of at least 90% therewith by deleting one or more amino acid residues from the 343- to 377-positions in SEQ ID NO: 1 or a region corresponding thereto and then inserting a peptide having from 2 to 15 amino acid residues into the deletion site; and a gene encoding the same. The above alkaline cellulase has an optimum pH value close to the pH value of laundry water and, therefore, is useful as an enzyme for detergents.

32 Claims, 3 Drawing Sheets

Fig. 1

```
Egl-237    1:MMLRKKTKQLISSILILVLLLSLFPAALAAEGNTREDNPKHLLGNDNVKRPSEAGALQLQEVDGQMTLVDQHGEKIQLRGMSTHGLQWFP  90
Egl-1139   1:MMLRKKTKQLISSILILVLLLSLFPPTALAAEGNTREDNPKHLLGNDNVKRPSEAGALQLQEVDGQMTLVDQHGEKIQLRGMSTHGLQWFP  90
Egl-64     1:MMLRKKTKQLISSILILVLLLSLFPPTALAAEGNTREDNPKHLLGNDNVKRPSEAGALQLQEVDGQMTLVDQHGEKIQLRGMSTHGLQWFP  90
Egl-N131b  1:MMLRKKTRQLGR-----------PAQA--EGNTREDNPKHLLGNDNVKRPSEAGALQLQEVDGQMTLVDQHGERIQLRGMSTHGLQWFP  76
             **********.............*....**************************************************

Egl-237    91:EILNDNAYKALSNDWDSNMIRLAMYVGENGYATNPELIKQRVIDGIELAIENDMYVIVDWHVHAPGDPRDPVYAGAKDFPREIAALYPNN  180
Egl-1139   91:EILNDNAYKALANDWESNMIRLAMYVGENGYASNPELIKSRVIKGIDLAIENDMYVIVDWHVHAPGDPRDPVYAGAEDPFRDIAALYPNN  180
Egl-64     91:EILNDNAYKALANDWESNMIRLAMYVGENGYASNPELIKSRVIKGIDLAIENDMYVIVDWHVHAPGDPRDPVYAGAEDFFRDIAALYPNN  180
Egl-N131b  77:EILNDNAYKALSNDWDSNMIRLAMYVGENGHATNPELIKQRVIDGIELAIENDMYVIVDWHVHAPGDPRDPVYAGAKDPFREIAALYPNN  166
              *********** *** ************** * ****** *** ** ****************************** **** *******

Egl-237    181:PHIIYELANEPSSNNNGGAGIPNNEEGWKAVKEYADPIVEMLRKSGNADDNIIIVGSPNWSQRPDLAADNPIDDHHTMYTVHFYTGSHAA  270
Egl-1139   181:PHIIYELANEPSSNNNGGAGIPNNEEGWNAVKEYADPIVEMLRDSGNADDNIIIVGSPNWSQRPDLAADNPIDDHHTMYTVHFYTGSHAA  270
Egl-64     181:PHIIYELANEPSSNNNGGAGIPNNEEGWNAVKEYADPIVEMLRDSGNADDNIIIVGSPNWSQRPDLAADNPIDDHHTMYTVHFYTGSHAA  270
Egl-N131b  167:PHIIYELANEPSSNNNGGAGIPNNEEGWKAVKEYADPIVQMLRKSGNADDNIIIVGSPNWSQRPDLAADNPIDDHHTMYTVHFYTGSHAA  256
               *************************** ********** .*** ***********************************************

Egl-237    271:STESYPSETPNSERGNVMSNTRYALENGVAVFATEWGTSQASGDGGPYFDEADVWIEPLNENNISWANWSLTNKNEVSGAFTPPFELGKSN  360
Egl-1139   271:STESYPPETPNSERGNVMSNTRYALENGVAVFATEWGTSQANGDGGPYFDEADVWIEPLNENNISWANWSLTNKNEVSGAFTPPFELGKSN  360
Egl-64     271:STESYPPETPNSERGNVMSNTRYALENGVAVFATEWGTSQANGDGGPYFDEADVWIEPLNENNISWANWSLTNKNEVSGAFTPPFELGKSN  360
Egl-N131b  257:STESYPPETPNSERGNVMSNTRYALENGVAVFATEWGTSQANGDGGPYFDEADVWIEPLNENNISWANWSLTNKNEVSGAFTPPFELGKSN  346
               ****** .******************************** . ********************************************

Egl-237    361:ATNLDPGPDHVWAPEELSLSGEYVRARIKGVNYEPIDRTKYTKVLWDFNDGTKQGFGVNSDSPNKELIAVDNENNTLKVSGLDVSNDVSD  450
Egl-1139   361:ATSLDPGPDQVWVPEELSLSGEYVRARIKGVNYEPIDRTKYTKVLWDFNDGTKQGFGVNGDSPVEDVVIEN-EAGALKLSGLDASNDVSE  449
Egl-64     361:ATSLDPGPDQVWVPEELSLSGEYVRARIKGVNYEPIDRTKYTKVLWDFNDGTKQGFGVNGDSPVEDVVIEN-EAGALKLSGLDASNDVSE  449
Egl-N131b  347:ATSLDPGPDQVWVPEELSLSGEYVRARIKGVNYEPIDRTKYTKVLWDFNDGTKQGFGVNSDSPNKELIAVDNENNTLKVSGLDVSNDVSD  436
               ** ****** ** ******************************************** ***       *   ** **** *****

Egl-237    451:GNFWANARLSANGWGKSVDILGAEKLTMDVIVDEPTTVAIAAIPQSSKSGWANPERAVRVNAEDFVQQTDGKYKAGLTITGEDAPNLKNI  540
Egl-1139   450:GNYWANARLSADGWGKSVDILGAEKLTMDVIVDEPTTVSIAAIPQGPSANWVNPNRAIKVEPTNPVPLED-KFKAELTITSADSPSLEAI  538
Egl-64     450:GNYWANARLSADGWGKSVDILGAEKLTMDVIVDEPTTVSIAAIPQGPSANWVNPNRAIKVEPTNFVPLGD-KFKAELTITSADSPSLEAI  538
Egl-N131b  437:GNFWANARLSANGWGKSVDILGAEKLTMDVIVDEPTTVAIAAIPQSSKSGWANPERAVRVNAEDFVQQTDGKYKAGLTITGEDAPSLEAI  526
               ** ******** *****************************  ****   * ** **    ** *  ** **** * * . *  .*

Egl-237    541:APHEEDNNMNNIILFVGTDAADVIYLDNIKVIGTEVEIPVVHDPKGEAVLPSVFEDGTROQGWDWAGESGVKTALTIEEANGSNALSWEFG  630
Egl-1139   539:AMHAENNNINNIILFVGTEGADVIYLDNIKVIGTEVEIPVVHDPKGEAVLPSVFEDGTRQGWDWAGESGVKTALTIEEANGSNALSWEFG  628
Egl-64     539:AMHAENNNINNIILFVGTEGADVIYLDNIKVIGTEVEIPVVHDPKGEAVLPSVFEDGTRQGWDWAGESGVKTALTIEEANGSNALSWEFG  628
Egl-N131b  527:AMHAENYTINNIILFVGTEGADVIYLDTIKVIGPEVEIPVVHDPKGEAVLPSVFEDGTROQGWDWAGESGVKTALTIEEANGSNALSWEFG  616
               * .*.*....********..******.******.************************************************************

Egl-237    631:YPEVKPSDNWATAPRLDFWKSDLVRGENDYVAFDPYLDPVRATEGAMNINLVFQPPTNGYWVQAPKTYTINFDELEEANQVNGLYHYEVK  720
Egl-1139   629:YPEVKPSDNWATAPRLDFWKSDLVRGENDYVTFDPYLDPVRATEGAMNINLVFQPPTNGYWVQAPKTYTINFDELEEPNQVNGLYHYEVK  718
Egl-64     629:YPEVKPSDNWATAPRLDFWKSDLVRGENDYVTFDPYLDPVRATEGAMNINLVFQPPTNGYWVQAPKTYTINFDELEEANQVNGLYHYEVK  718
Egl-N131b  617:YPEVKPSDNWATAPRLDFWKSDLVRGENDYVTFDPYLDPVRATEGAMNINLVFQPPTNGYWVQAPKTYTINFDELEEANQVNGLYHYEVK  706
               ******************************. ********************************************. ***********

Egl-237    721:INVRDITNIQDDTLLRNMMIIFADVESDFAGRVPVDNVRFEGAATTEPVEPEPVDPGEETPPVDEKEAKKEQKEAEKEEKEAVKEEKKEA  810
Egl-1139   719:INVRDITNIQDDTLLRNMMIIFADVESDFAGRVPVDNVRFEGAATTEPVEPEPVDPGEETPPVDEKEAKTEQKEAEKEEKEE--------  800
Egl-64     719:INVRDITNIQDDTLLRNMMIIFADVESDFAGRVPVDNVRFEGAATTEPVEPEPVDPGEETPPVDEKEAKKEQKEAEKEEKEAVKEEKKEA  808
Egl-N131b  707:INVRDITNIQDDTLLRNMMIIFADVESDFAGRVPVDNVRFEGAATTEPVEPEPVDPGEETPPVDEKEAKKEQKEAEKEEKEAVKEEKKEA  796
               **********************************************************************. *********** .********

Egl-237    811:KEEKKAVKNEAKKK                                                                            824
Egl-1139   801:--------------                                                                            801
Egl-64     809:KEEKKAIKNEATKK                                                                            822
Egl-N131b  797:KEEKKAIKNEATKK                                                                            810
               ....... .... ..
```

MUTATED ALKALINE CELLULASE

TECHNICAL FIELD

The present invention relates to mutated alkaline cellulases which can be incorporated in laundry detergents or the like.

BACKGROUND ART

When a laundry detergent is used for washing laundry, the pH of the washing liquid is mostly from 10 to 11; i.e., within an alkaline range. Therefore, an enzyme to be incorporated into laundry detergents is required to exhibit an optimum pH in an alkaline region and to be stable under an alkaline condition.

Conventionally known alkaline cellulases which can be incorporated into laundry detergents or other detergents include alkaline cellulase derived from *Bacillus* sp. KSM-635 belonging to *Bacillus* (Japanese Patent Publication (kokoku) No. 60-23158, Japanese Patent Publication (kokoku) No. 6-030578, U.S. Pat. No. 4,945,053, etc.); alkaline cellulase derived from *Bacillus* sp. KSM-64 (Shikata et al. *Agric. Biol. Chem.*, 54, 91-96, 1990, Sumitomo et al., *Biosci. Biotechnol. Biochem.*, 56, 872-877, 1992); heat-resistant alkaline cellulase produced from mesophilic and alkaliphilic fungi, *Bacillus* sp. KSM-S237 (FERM-BP7875: deposited on Feb. 6, 1997 with Independent Administrative Institution of National Institute of Advanced Industrial Science and Technology, International Patent Organism Depositary (Tsukuba Central 6, 1-1-1 Higashi, Tsukuba, Ibaraki, Japan (postal code 305-8566))) (Japanese Patent Application Laid-Open (kokai) No. 10-313859); alkaline cellulase derived from *Bacillus* sp. KSM-N257 (Japanese Patent Application No. 12-281378); and alkaline cellulase derived from *Bacillus* sp. KSM-N131 (Japanese Patent Application No. 12-373859). However, in the case where the substrate is carboxymethylcellulose (CMC) these alkaline cellulases exhibit an optimum reaction pH of about 9; therefore, the cellulases do not have the optimum pH under conditions encountered during laundry washing.

In the meanwhile, a study has been done on changing the optimum reaction pH of a glucosidase. The study shows that the optimum pH of a glucosidase is shifted from alkali to neutral by constructing a chimeric protein from an alkaline (NK1) cellulase derived from alkaliphilic *Bacillus* and neutral cellulase (BSC) derived from *Bacillus subtilis* (Park et al. *Protein Enz.* 6, 921-926, 1993).

Recently, it has been reported that the optimum pH of cellobiohydrolase (Cel7A) derived from *Trichoderma reesei* was increased as compared with that of its wild-type strain by substitution of amino acid residues in the vicinity of its active center (Beker et al, *Biochem. J.*, 356, 19-31, 2001). However, in this case, the optimum pH of the wild-type enzyme falls within an acidic range, and the increase in the optimum pH of the mutant is within 1 pH unit or less.

Thus, there has been substantially no report in which the optimum reaction pH of glucosidase is shifted toward the alkaline side.

The present invention is directed to the provision of a mutated alkaline cellulase having an optimum pH as an enzyme to be incorporated into detergent, which is obtained by modifying the alkaline cellulase gene.

DISCLOSURE OF THE INVENTION

The present inventors have searched enzymes which can attain the above purpose by estimating the three-dimensional structure of an alkaline cellulase having an amino acid sequence represented by SEQ ID NO: 2 (Egl-237); in particular, the structure of its active domain, and by incorporating mutations through site-specific mutation. As a result, the present inventors have found that the optimum reaction pH in the CMC decomposition activity can be increased by deleting amino acid residues in a specific region which forms a portion of the loop structure and inserting a peptide into the position.

Accordingly, the present invention provides a mutated alkaline cellulase obtained by deleting, from a cellulase having an amino acid sequence represented by SEQ ID NO: 2 or an amino acid sequence exhibiting at least 90% homology therewith, one or more amino acid residues chosen from the 343rd to 377th positions in SEQ ID NO: 2 or from corresponding positions, and inserting a peptide having 2 to 15 amino acid residues into at least one of the deleted positions; as well as a gene encoding the mutated alkaline cellulase.

The present invention also provides a vector containing the gene, and a transformant containing the vector.

BRIEF DESCRIPTION OF THE DRAWINGS

FIGS. 1a to 1c show aligned amino acid sequences of cellulases having at least 90% homology with the amino acid sequence represented by SEQ ID NO: 2 (Egl-237). Egl-1139 appears as SEQ ID NO: 7, Egl-64 appears as SEQ ID NO: 8, and Egl-N131b appears as SEQ ID NO: 9.

BEST MODE FOR CARRYING OUT THE INVENTION

Figure 2:
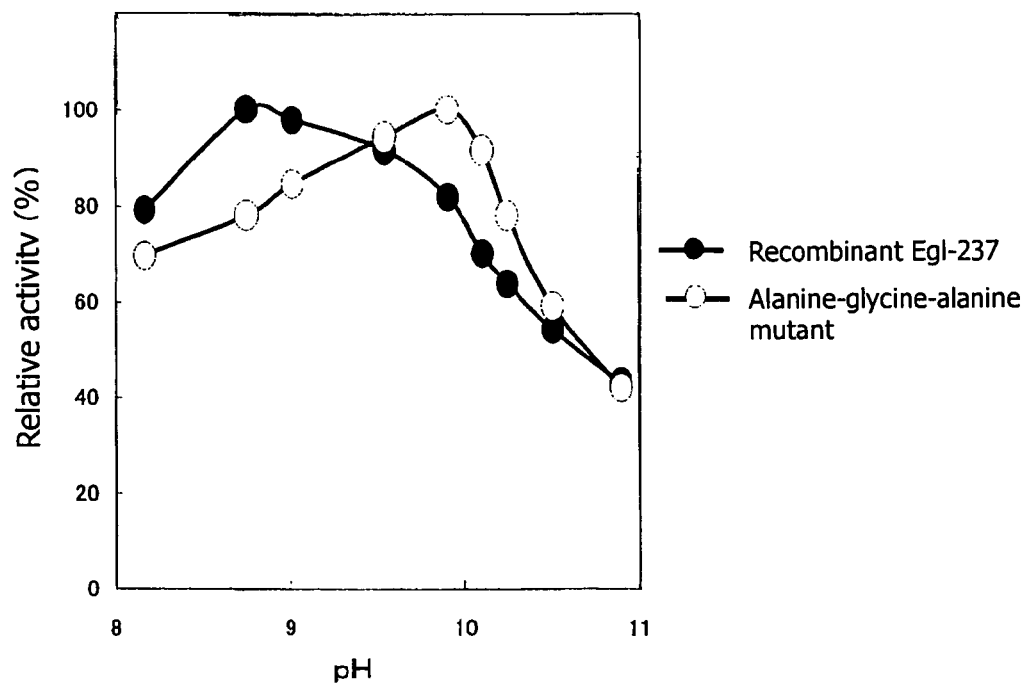
FIG. 2 shows the optimum reaction pH of the alkaline cellulase which has been mutated through use of alanine-glycine-alanine.

The mutated alkaline cellulases according to the present invention are obtained by using, as a cellulase to be mutated (hereinafter may be referred to as "parent alkaline cellulase"), a cellulase having an amino acid sequence represented by in SEQ ID NO: 2 or an amino acid sequence exhibiting at least 90% homology therewith, and by deleting one or more amino acid residues chosen from the 343rd to 377th positions in SEQ ID NO: 2 or from corresponding positions and inserting a peptide having 2 to 15 amino acid residues into at least one of the deleted positions. The parent alkaline cellulases may be obtained either through spontaneous or artificial mutation of the cellulase having the amino acid sequence of SEQ ID NO: 2.

The parent cellulase exhibiting 90% or more homology with the amino acid sequence represented by SEQ ID NO: 2 preferably exhibits 95% or more homology, more preferably 98% or more homology, with the amino acid sequence. The cellulase may be of wild-type or a mutant of a wild-type cellulase. The homology of an amino acid sequence can be calculated by means of a program such as maximum matching or search homology of GENETYX-WIN (Software Development Co.).

When the molecular structure of the cellulase exhibiting 90% or more homology with the amino acid sequence represented by SEQ ID NO: 2 is estimated through a homology modeling technique and by means of 3D-1D, XPLORE, and PROCHECK programs, the cellulase preferably has the following two characteristics; (i) the cellulase has an amino acid sequence exhibiting 70% or more homology, more preferably 80% or more homology, much more preferably 90% or more homology, still more preferably 95% or more homology, yet still more preferably 98% or more homology, with the region from the 42nd position to the 404th position (valine) (i.e., the active domain region) (i.e., the active domain region) of SEQ ID NO: 2; and (ii) the region from the 343rd position (asparagine) to the 377th position (leucine) of SEQ ID NO: 2 has a loop structure in the cellulase molecule. The homology of an amino acid sequence may be calculated in accordance with, for example, the Lipman-Pearson method (*Science*, 227, 1435, 1985).

In addition, the parent alkaline cellulase preferably has characteristics such as the followings: having a molecular weight of 86,000±2,000 as measured through sodium dodecyl sulfate polyacrylamide gel electrophoresis (SDS-PAGE) or gel filtration; having an optimum reaction pH of from 7.5 to 9.0 in the case where the substrate is carboxymethylcellulose; and having an optimum reaction temperature falling within a range of from 40 to 50° C. In addition, it is preferable that the parent alkaline cellulase effectively digests lichenan as well as carboxymethylcellulose and sufficiently maintains a stability when treated at pH 9 and at 50° C. for 10 minutes.

More preferably, the parent alkaline cellulase has the following characteristics: having a molecular weight of 86,000±2,000 (as measured through SDS-PAGE or gel filtration employing a Sephacryl S200 column); having an optimum reaction pH of from 8.6 to 9.0 and an optimum reaction temperature of 50° C.; effectively digesting lichenan as well as carboxymethylcellulose; exhibiting a remaining activity of 95% or more, where the remaining activity after treatment at 30° C. for 10 minutes is taken as 100%, after being treated at pH 9 and 50° C. for 10 minutes in the presence of 5 mM calcium chloride.

Accordingly, the parent alkaline cellulase of the present invention is preferably, in addition to the alkaline cellulase having the amino acid sequence represented by SEQ ID NO: 2, an alkaline cellulase having (i) the above amino acid sequence features-i.e., having a high homology in the active domain region of SEQ ID NO: 2 and containing a particular region having a loop structure in the cellulase molecule as described above-and/or the above enzymatic characteristics (particularly preferably, having the amino acid sequence features and the enzymatic characteristics in combination), and (ii) an amino acid sequence exhibiting 90% or more homology (preferably 95% or more homology, much more preferably 98% or more homology) with that represented by SEQ ID NO: 2.

Examples of the parent alkaline cellulase of the present invention include Egl-237 [derived from *Bacillus* sp. KSM-S237 (FERM BP-7875), which is "alkaline cellulase having the amino acid sequence represented by SEQ ID NO: 2," Hakamada et al., *Biosci. Biotechnol. Biochem.*, 64, 2281-2289, 2000]; alkaline cellulases derived from *Bacillus* sp. strain 1139 (Egl-1139; SEQ ID NO: 7) (Fukumori et al., *J. Gen. Microbiol.*, 132, 2329-2335) (homology: 91.4%); alkaline cellulases derived from *Bacillus* sp. strain KSM-64 (Egl-64; SEQ NO: 8) (Sumitomo et al., *Biosci. Biotechnol. Biochem.*, 56, 872-877, 1992) (homology: 91.9%); and cellulases derived from *Bacillus* sp. strain KSM-N131 (Egl-N131b; SEQ ID NO: 9) (Japanese Patent Application No. 2000-47237) (homology: 95.0%).

The mutated alkaline cellulase of the present invention is obtained by deleting, from the parent alkaline cellulase, one or more amino acid residues chosen from the 343rd to 377th positions in SEQ ID NO: 2 or from corresponding positions and inserting a peptide having 2 to 15 amino acid residues into at least one of the deleted positions.

The amino acid residue(s) to be deleted may be any of 35 amino acid residues included in the 343rd to 377th positions of SEQ ID NO: 2. The number of the amino acid residue(s) to be deleted may be any of 1 to 35. The amino acid residues to be deleted are continuous or non-continuous. The amino acid residue(s) to be deleted is(are) preferably included in the 350th to 377th positions, more preferably in the 355th to 365th positions, much more preferably in the 357th to 362nd positions, of SEQ ID NO: 2.

More preferably, the amino acid residue(s) to be deleted is(are) any 1 to 27 residues, any 2 to 15 residues, or any 3 to 10 residues contained in the 343rd to 377th positions; any 1 to 8 residues, any 3 to 6 residues, or all the amino acid residues contained in the 355th to 377th positions; and any 2 residues, any 2 to 5 residues, or all the amino acid residues contained in the 357th to 362nd positions.

Three-dimensional structural analysis through homology modeling (Ozawa ei al., *Protein Eng.*, 14, 501-504, 2001) suggests that the amino acid region at the 343rd to 377th positions of SEQ ID NO: 2 is located relatively distant from the active center of Egl-237 and therefore has a high degree of freedom, and is suggested to be a region that forms a portion of the loop structure that is intimately involved in maintaining the cellulase structure.

The "amino acid residue corresponding to the 343rd to 377th positions of SEQ ID NO: 2" can be identified by comparing amino acid sequences by means of a known algorithm such as Lipman-Pearson's method, and aligning the amino acid residues contained in the amino acid sequences of the alkaline cellulases such that the homology of each amino acid sequence with respect to that of SEQ ID NO: 2 is maximized. By aligning the amino acid sequence of the cellulase in such a manner, the position of the homologous amino acid residue in the amino acid sequence of each cellulase can be determined, irrespective of insertion or deletion in the amino acid sequence (FIG. 1). The homologous position is presumed to exist at the same three-dimensional position and to bring about similar effects with regard to a specific function of the target cellulase.

Table 1 shows the positions of Egl-1139 (SEQ ID NO: 7), Egl-64 (SEQ ID NO: 8), and Egl-N131b (SEQ ID NO: 9) corresponding to the 357th to 362nd positions of alkaline cellulase having an amino acid sequence represented by SEQ ID NO: 2 (Egl-237).

TABLE 1

| Egl-237 | Egl-1139 | Egl-64 | Egl-N131b |
|---------|----------|--------|-----------|
| 357Gly  | 357Gly   | 357Gly | 343Gly    |
| 358Lys  | 358Lys   | 358Lys | 344Lys    |
| 359Ser  | 359Ser   | 359Ser | 345Ser    |
| 360Asn  | 360Asn   | 360Asn | 346Asn    |
| 361Ala  | 361Ala   | 361Ala | 347Ala    |
| 362Thr  | 362Thr   | 362Thr | 348Thr    |

The peptide to be inserted into the deleted position(s) may be formed of any of 20 essential amino acids. The peptide preferably contains alanine, glycine, histidine, or arginine.

More preferably, the peptide contains alanine and glycine, alanine and histidine, or alanine and arginine.

The number of the amino acid residues forming the peptide to be inserted is preferably from 2 to 15, more preferably from 2 to 10, much more preferably from 2 to 6, particularly preferably 3.

Preferred examples of the peptide to be inserted include asparagine-threonine-alanine-valine-glycine-isoleucine, alanine-serine-methionine-leucine-phenylalanine-glutamic acid, cysteine-leucine-glycine-histidine-serine, tyrosine-glutamine-lysine-alanine-alanine, aspartic acid-methionine-isoleucine-valine, isoleucine-threonine-proline-lysine, glycine-leucine-cysteine, and serine-valine-phenylalanine, inter alia, a peptide containing alanine residues at both ends thereof and having 3 to 6 residues; more preferably alanine-any one amino acid-alanine; even more preferably alanine-glycine-alanine, alanine-histidine-alanine, or alanine-arginine-alanine.

The mutated alkaline cellulases of the present invention encompasses those having one to several amino acid residues deleted, replaced, or added at position(s) in the amino acid sequence other than the mutated position(s) described above, so far as they do not lose their alkaline cellulase activity and the modified characteristics described above.

The mutated alkaline cellulase of the present invention may be obtained through incorporating a desired mutation into a parent alkaline cellulase in a manner, for example, described below.

Specifically, a parent alkaline cellulase is cultured, and the resultant culture broth is centrifuged, to thereby isolate cells. Through use of the alkaline cellulase gene collected from the cells, a chromosomal DNA containing the alkali cellulase gene is prepared [through, for example, a method of Marmar (*J. Mol. Biol.,* 3, 208-212, 1961) or a method of Saito and Miura (*Biochim. Biophys. Acta,* 72, 619-629, 1963)]. The chromosomal DNA may be subjected to cloning through shotgun cloning or PCR, to thereby prepare a gene (SEQ ID NO: 1) encoding the parent alkaline cellulase (e.g., alkaline cellulase having an amino acid sequence represented by SEQ ID NO: 2). To the thus-obtained gene, a mutation is introduced, and the resultant mutated gene is incorporated to a plasmid. Appropriate host cells are transformed through use of the plasmid and then cultured, and the mutated alkaline cellulase of the present invention may be collected from the culture.

Examples of the method which may be employed to introduce a mutation into a gene encoding a parent alkaline cellulase, include site-specific mutation. For example, a Site-Directed Mutagenesis System Mutan-Super Express Km kit (product of Takara) may be used. The mutated alkaline cellulase gene may be incorporated into an appropriate vector.

The vector may be any vector which satisfies the following three conditions: (i) the vector can be replicated and maintained in host cells; (ii) the vector allows expression of the alkaline cellulase gene; and (iii) the vector can stably maintain the gene incorporated therein. When the host cell is a bacterium belonging to *Bacillus*, examples of the vector to be used include pUB110 and pHY300PLK. When the host cell is *E. coli*, examples of the vector to be used include pUC18, pUC19, pBR322, and pHY300PLK.

Transformation of the host bacteria through use of the thus-obtained recombinant vector may be carried out through, for example, the protoplast method, the competent cell method, or the electroporation. Examples of the host bacteria include, but are not limited to, gram-positive bacteria such as those belonging to *Bacillus* sp. (*Bacillus subtilis*), gram-negative bacteria such as *Escherichia coli*, fungi such as those belonging to *Streptomyces* (Actinomycetes), to *Saccharomyces* (yeast), and to *Aspergillus* (molds).

The thus-obtained transformant may be cultured under proper conditions using a medium containing an assimilable carbon source, nitrogen source, metal salt, vitamin, etc. The enzyme is isolated from the thus-obtained culture broth and then purified through a routine method, followed by lyophilization, spray drying, or crystallization to obtain the enzyme in a desired form.

The thus-obtained mutated alkaline cellulase has an optimum reaction pH higher than that of the parent alkaline cellulase. The optimum reaction pH lies preferably within 9.0 to 9.5, more preferably within 9.5 to as high as 10.0. In addition, other than the optimum reaction pH, the mutated alkaline cellulase preferably has the same characteristics as the parent alkaline cellulase.

EXAMPLES

Example 1

Modification of Loop Region of Egl-237

The molecule model of Egl-237 was constructed through homology modeling based on the analytical data of CelK, whose crystal structure had already been analyzed. Details of the model structure were determined by means of 3D-1D, XPLORE, and PROCHECK programs. Thereafter, on the basis of the obtained data, amino acid residues contained in a portion of the loop structure (from the 357th (glycine) to 362nd (threonine)) were deleted, and one of alanine-glycine-alanine, alanine-histidine-alanine, and alanine-arginine-alanine was inserted to the deleted position. Mutation of the loop region was performed through use of mutation introducing primers 1, 2, and 3 (SEQ ID NOs: 3, 4, and 5), respectively, and through use of mutation introducing primer 4 (SEQ ID NO: 6) as an antisense primer. When alanine-glycine-alanine was inserted for mutation, Egl-237 gene was incorporated into pHY300PLK, and the product was employed as a template DNA. When alanine-histidine-alanine or alanine-arginine-alanine was inserted for mutation, a plasmid composed of pHY300PLK containing a gene mutated by alanine-glycine-alanine was employed as a template DNA. Specifically, after mixing of 0.5 µL (10 ng) of the template DNA plasmid, 20 µL (1 µM) of the mutation introducing primer, 20 µL (1 µM) of the antisense primer, 10 µL of a ×10 PCR buffer solution, 8 µL of a 10 mM deoxynucleotide triphosphate (dNTP) mixture, 0.5 µL (2.5 units) of "Pyrobest DNA polymerase" (product of Takara), and 39.5 µL of deionized water, PCR was carried out by "gene amp PCR system 9700" (product of Amersham-Pharmacia). The reaction conditions were as follows; starting with thermal denaturation at 94° C. for 2 minutes; followed by 30 cycles of 94° C. for 1 minute; 60° C. for 1 minute; 72° C. for 1.5 minutes; and finally 72° C. for 3 minutes. After purification of the resultant PCR product by "GFX PCR DNA and Gel Band Purification Kit" (Amersham-Pharmacia) (43.5 µL), 5.5 µL of a ×10 phosphorylation buffer and 1 µL (10 units) of polynucleotide kinase were added to the solution, and it was maintained at 37° C. for 1 hour for phosphorylation, followed by purification. After mixing 25 µL of the phosphorylated PCR product with 2 µL (20 ng) of the template plasmid, 10 µL of a ×10 PCR buffer, 8 µL of a 10 mM dNTP mixture, 1 µL (5 units) of "Pyrobest DNA polymerase," and 54 µL of deionized water, PCR was conducted. The reaction conditions were as follows; starting with thermal denaturation at 94° C. for 2 minutes; followed by 30 cycles of 94° C. for 1 minute; 58° C. for 1 minute; 72° C. for 6 minutes; and finally 72° C. for 12 minutes. The resultant PCR product was purified (43.5 μL). Then, 5.5 μL of a ×10 phosphorylation buffer and 1 μL (10 units) of polynucleotide kinase were added thereto, and phosphorylation was conducted at 37° C. for 1 hour. The mixture was subjected to ethanol precipitation. The thus-collected DNA solution (10 μL) was subjected to ligation at 16° C. for 18 hours by use of a ligation kit ver. 2 (product of Takara) for self ring closure, followed by another round of ethanol precipitation, whereby the DNA mixture was collected.

Example 2

Method for Transformation

By use of 5 μL of the DNA mixture obtained in Example 1, the DNA was introduced into the *Bacillus subtilis* strain ISW1214, whereby the corresponding transformant was obtained (Chang and Cohen, *Mol. Gen. Gent.*, 168, 111, 1979). The thus-obtained protoplast was inoculated onto a DM3 regeneration agar medium [0.8% (w/v) agar (product of Wako Pure Chemicals), 0.3M disodium succinate 6 hydrate, 0.5% "Casamino Acids Technical" (product of Difco), 0.5% yeast extract, 0.35% $KH_2PO_4$, 0.15% $K_2HPO_4$, 0.5% glucose, 0.4% $MgCl_2.6H_2O$, 0.01% bovine serum albumin (product of Sigma), 0.5% CMC (Kanto Chemical Co., Inc.), 0.005% trypan blue (product of Merck), and an amino acid mixture (leucine and methionine, 10 μg/mL)] containing tetracycline (15 μg/mL, Sigma), and incubated at 30° C. for 72 hours to obtain a transformant. The transformant that formd a halo on the DM3 regeneration agar plate was cultured while shaking at 30° C. for 15 hours in a polypeptone medium (3% polypeptone S, 3% maltose, 0.5% fish meat extract (product of Wako Pure Chemicals), 0.1% yeast extract, 0.1% $KH_2PO_4$, and 0.02% $MgSO_4.7H_2O$) containing tetracycline (15 μg/mL). After collection of the cells, plasmids were extracted and purified by "Micro Prep Plasmid Purification kit" (product of Amersham-Pharmacia). The mutated nucleotide sequence of the cellulase gene, which had been inserted into the plasmids, was confirmed by means of "377DNA Sequencer" (product of Applied Biosystems). The nucleotide sequencing was performed through use of primers which were suitable for determining nucleotide sequences in the vicinity of the mutated position, and screening was performed, whereby plasmids to which the target mutation had been incorporated were obtained.

Example 3

Production of Cellulase Mutant

The host bacteria *B. Subtilis* strain ISW1214 was cultured at 30° C. for 72 hours in a medium containing 3% polypepton S (product of Nihon Pharmaceutical), 0.5% fish meat extract, 0.05% yeast extract, 0.1% $KH_2PO_4$, 0.02% $MgSO_4.7H_2O$, tetracycline (15 μg/mL), and 5% maltose.

After completion of culturing of various cellulase mutants, the cellulose activity of variants having a loop structure mutated by alanine-glycine-alanine, alanine-histidine-alanine, and alanine-arginine-alanine were found as 36800 U/L, 34700 U/L, and 32400 U/L, respectively.

The cellulase activity was determined through the 3,5-dinitrosalicylic acid (DNS) method.

That is, to a reaction mixture composed of 0.2 mL of a 0.5M glycine-sodium hydroxide buffer (pH 9.0), 0.4 mL of 2.5% (w/v) carboxymethyl cellulose (A01MC: Nippon Paper Industries), and 0.3 mL of deionized water, 0.1 mL of a properly diluted enzyme solution was added. After the resultant mixture was allowed to undergo reaction at 40° C. for 20 minutes, 1 mL of a dinitrosalicylic acid reagent (0.5% dinitrosalicylic acid, 30% Rochelle Salt, 1.6% aqueous sodium hydroxide) was added, and the color of a reducing sugar was developed in boiling water for 5 minutes. After quenching in ice water, 4 mL of deionized water was added, and absorbance at 535 nm was measured to determine the production amount of the reducing sugar. A blank sample was prepared as follows; dinitrosalicylic acid reagent was added to the reaction mixture that had been treated as described except the addition of the enzyme solution. Then the enzyme solution was added thereto, and the color was developed in the same way. One unit (1 U) of an enzyme activity was defined as an amount of enzyme which produces a reducing sugar in an amount equivalent to 1 μmol of glucose in 1 minute under the above-described reaction conditions.

Example 4

Purification of Recombinant Loop-modified Cellulase

The supernatant of the culture broth containing the recombinant loop-modified cellulase was diluted 10-fold with deionized water, and the diluted supernatant was incorporated into a column (2.5 cm×5 cm) containing DEAE Toyopearl (Tosoh Corporation) that had been pre-equilibrated with 10 mM Tris-HCl buffer (pH 8.0). The column was washed further with the buffer, and protein was eluted with a linear gradient of from 0 to 0.4M solution of sodium chloride solution (400 mL) in the same buffer. The recombinant loop-modified cellulase of interest was eluted at a sodium chloride solution concentration of approximately 0.25 M and the eluted component was found substantially homogenous as analyzed by electrophoresis. Desalting and condensation were performed through use of an ultrafilter (PM10, Millipore).

Example 5

Optimum Reaction pH of Recombinant Loop-modified Cellulase

Figure 3:
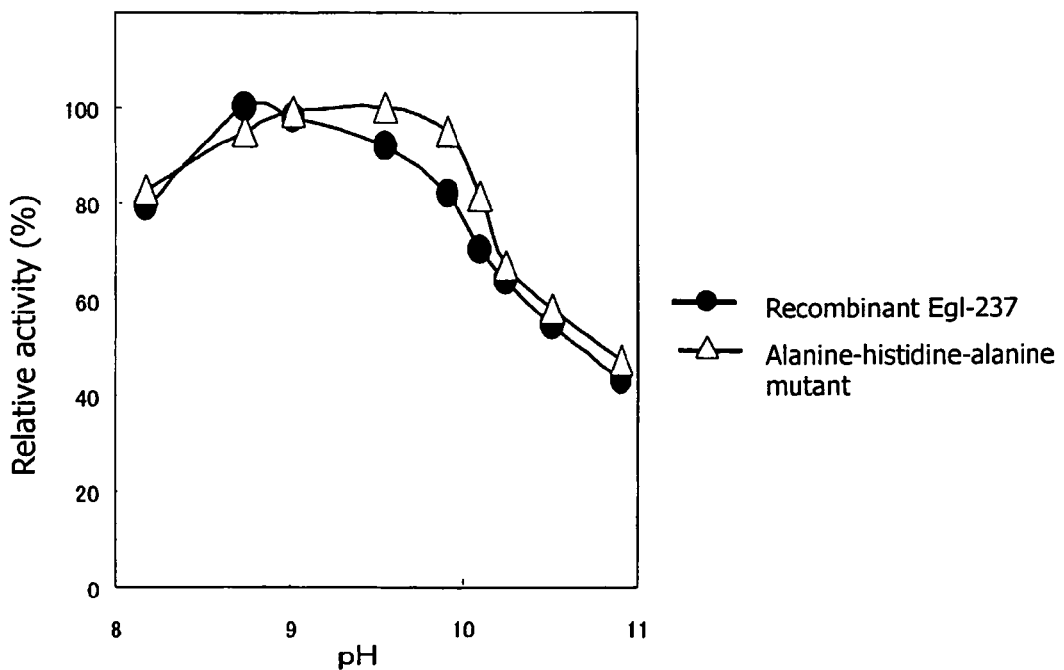
FIG. 3 shows the optimum reaction pH of the alkaline cellulase which has been mutated through use of alanine-histidine-alanine.
Figure 4:
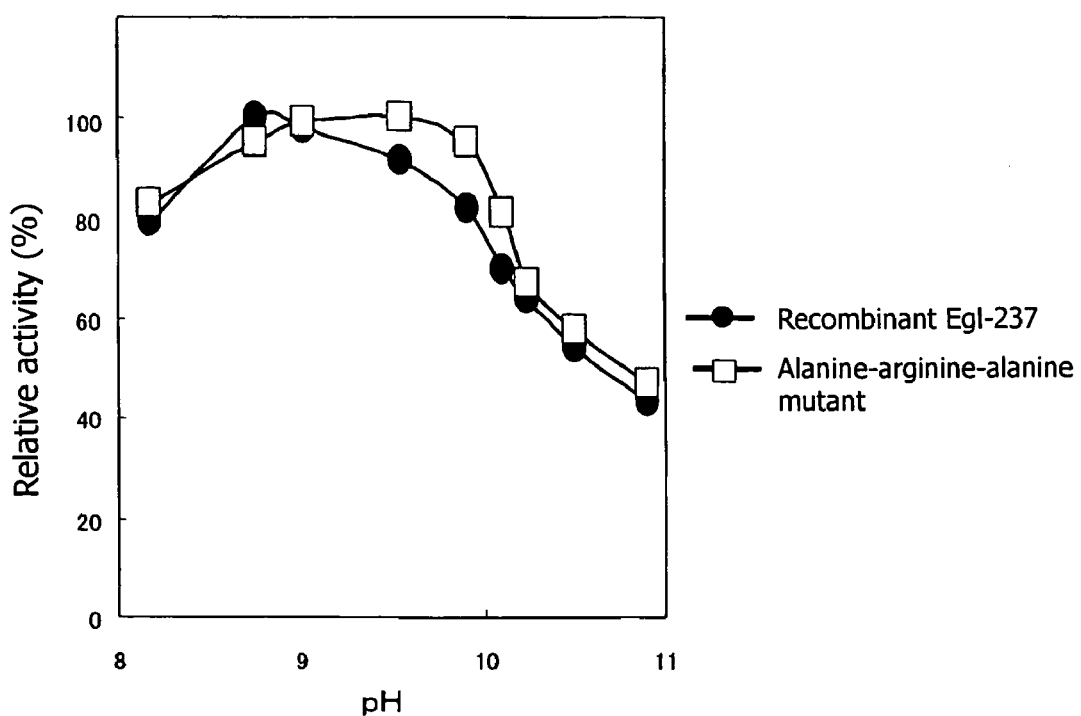
FIG. 4 shows the optimum reaction pH of the alkaline cellulase which has been mutated through use of alanine-arginine-alanine.

The purified product of the recombinant loop-modified cellulase prepared in Example 4 was investigated in terms of the effect of pH on enzymatic reaction. Optimum reaction pH was determined by use of glycine-sodium hydroxide buffer (pH 8.2 to 10.9). As a result, a recombinant wild-type cellulase was found to have an optimum reaction pH of 9.0, whereas the cellulase which had been modified by alanine-glycine-alanine was found to have an optimum reaction pH of 10, which is 1 pH unit higher than that of the recombinant wild-type cellulase (FIG. 2); i.e., the optimum pH shifted toward higher alkaline side. The cellulase, which had been modified by alanine-histidine-alanine or alanine-arginine-alanine was found to have an optimum reaction pH of about 9.6. In addition, within a range of pH 8.8 to pH 9.9, the cellulase which had been modified by alanine-histidine-alanine or alanine-arginine-alanine was found to have a relative activity (i.e., a percent activity when the activity at optimum reaction pH, in this case, pH 9.6, is taken as 100%) of 95% or more, which is higher than those of the parent cellulase and the cellulase mutated by alanine-glycine-alanine (FIGS. 2 and 3).

INDUSTRIAL APPLICABILITY

The mutated alkaline cellulases of the present invention have an optimum pH near the pH of the washing liquid (pH of about 10.5), and thus are useful as enzymes for detergents.

The invention claimed is:
1. A mutated alkaline cellulase which is obtained by deleting, from a cellulase having the amino acid sequence of SEQ ID NO: 2 or a homologous amino acid sequence exhibiting at least 95% sequence homology therewith, a peptide consisting of one or more amino acid residues chosen from the 357$^{th}$ to 362$^{nd}$ positions in SEQ ID NO: 2 or from corresponding positions of said homologous amino acid sequence and replacing the peptide with an insertion peptide selected from the group consisting of:
asparagine-threonine-alanine-valine-glycine-isoleucine,
alanine-serine-methionine-leucine-phenylalanine-glutamic acid,
cysteine-leucine-glycine-histidine-serine,
tyrosine-glutamine-lysine-alanine-alanine,
aspartic acid-methionine-isoleucine-valine,
isoleucine-threonine-proline-lysine,
glycine-leucine-cysteine,
serine-valine-phenylalanine, and
a peptide containing alanine residues at both ends thereof and having 3 to 6 residues, wherein said mutated alkaline cellulase has alkaline cellulase activity.

2. The mutated alkaline cellulase as described in claim 1, wherein said insertion peptide containing alanine residues at both ends thereof and having 3 to 6 residues, contains as structural amino acid residues thereof, alanine and glycine, alanine and histidine, or alanine and arginine.

3. The mutated alkaline cellulase as described in claim 1, wherein said insertion peptide is selected from the group consisting of alanine-glycine-alanine, alanine-histidine-alanine, and alanine-arginine-alanine.

4. An isolated polynucleotide encoding a mutated alkaline cellulase as recited in claim 1.

5. A recombinant vector comprising the polynucleotide as recited in claim 4.

6. An isolated transformed microorganism comprising a recombinant vector as recited in claim 5.

7. A method for producing a mutated alkaline cellulase, which comprises culturing the isolated transformed microorganism of claim 6 in a medium for a time and under conditions suitable to produce and accumulate said mutated alkaline cellulase, and isolating said mutated alkaline cellulase.

8. The mutated alkaline cellulase as described in claim 1, wherein the homologous amino acid sequence exhibits at least 98% sequence homology to the amino acid sequence of SEQ ID NO: 2.

9. A mutated alkaline cellulase which is obtained by deleting, from a cellulase selected from the group consisting of SEQ ID NO: 7, SEQ ID NO: 8, and SEQ ID NO: 9, a peptide consisting of one or more amino acid residues chosen from the positions corresponding to the $357^{th}$ to $362^{nd}$ positions of SEQ ID NO: 2, and replacing the peptide with an insertion peptide having 2 to 6 amino acid residues, wherein said mutated alkaline cellulase has alkaline cellulase activity.

10. The mutated alkaline cellulase according to claim 9, wherein said insertion peptide has 2 to 5 amino acid residues.

11. The mutated alkaline cellulase as described in claim 9, wherein said insertion peptide has 3 amino acid residues.

12. The mutated alkaline cellulase as described in claim 9, wherein said insertion peptide contains as structural amino acid residues thereof, alanine and glycine, alanine and histidine, or alanine and arginine.

13. The mutated alkaline cellulase as described in claim 9, wherein said insertion peptide is selected from the group consisting of alanine-glycine-alanine, alanine-histidine-alanine, and alanine-arginine-alanine.

14. An isolated polynucleotide encoding a mutated alkaline cellulase as recited in claim 9.

15. A recombinant vector comprising the polynucleotide as recited in claim 14.

16. An isolated transformed microorganism comprising a recombinant vector as recited in claim 15.

17. A method for producing a mutated alkaline cellulase, which comprises culturing the isolated transformed microorganism of claim 16 in a medium for a time and under conditions suitable to produce and accumulate said mutated alkaline cellulase, and isolating said mutated alkaline cellulase.

18. The mutated alkaline cellulase as described in claim 9, wherein said insertion peptide is selected from the group consisting of:
asparagine-threonine-alanine-valine-glycine-isoleucine,
alanine-serine-methionine-leucine-phenylalanine-glutamic acid,
cysteine-leucine-glycine-histidine-serine,
tyrosine-glutamine-lysine-alanine-alanine,
aspartic acid-methionine-isoleucine-valine,
isoleucine-threonine-proline-lysine,
glycine-leucine-cysteine, and
serine-valine-phenylalanine.

19. A method of producing a mutated alkaline cellulase comprising deleting from a cellulase having the amino acid of sequence of SEQ ID NO: 2 or a homologous amino acid sequence exhibiting at least 95% sequence homology therewith, a peptide consisting of one or more amino acid residues chosen from the $357^{th}$ to $362^{nd}$ positions in SEQ ID NO: 2 or from corresponding positions of said homologous amino acid sequence and replacing the peptide with an insertion peptide having 2 to 6 amino acid residues, wherein said mutated alkaline cellulase has alkaline cellulase activity.

20. The method of claim 19, wherein said insertion peptide is selected from the group consisting of:
asparagine-threonine-alanine-valine-glycine-isoleucine,
alanine-serine-methionine-leucine-phenylalanine-glutamic acid,
cysteine-leucine-glycine-histidine-serine,
tyrosine-glutamine-lysine-alanine-alanine,
aspartic acid-methionine-isoleucine-valine,
isoleucine-threonine-proline-lysine,
glycine-leucine-cysteine, and
serine-valine-phenylalanine.

21. The method of claim 19, wherein said insertion peptide has 2 to 5 amino acid residues.

22. The method of claim 19, wherein said insertion peptide has 3 amino acid residues.

23. The method of claim 19, wherein said insertion peptide contains alanine residues at both ends thereof and has 3 to 6 residues.

24. The method of claim 19, wherein said insertion peptide contains as structural amino acid residues thereof, alanine and glycine, alanine and histidine, or alanine and arginine.

25. The method of claim 19, wherein said insertion peptide is selected from the group consisting of alanine-glycine-alanine, alanine-histidine-alanine, and alanine-arginine-alanine.

26. A method of producing a mutated alkaline cellulase comprising deleting from a cellulase selected from the group consisting of SEQ ID NO: 7, SEQ ID NO: 8, and SEQ ID NO: 9, a peptide consisting of one or more amino acid residues chosen from the positions corresponding to the $357^{th}$ to $362^{nd}$ positions of SEQ ID NO: 2, and replacing the peptide with an insertion peptide having 2 to 6 amino acid residues, wherein said mutated alkaline cellulase has alkaline cellulase activity.

27. The method of claim 26, wherein said insertion peptide is selected from the group consisting of:
asparagine-threonine-alanine-valine-glycine-isoleucine,
alanine-serine-methionine-leucine-phenylalanine-glutamic acid,
cysteine-leucine-glycine-histidine-serine,
tyrosine-glutamine-lysine-alanine-alanine,
aspartic acid-methionine-isoleucine-valine,
isoleucine-threonine-proline-lysine,
glycine-leucine-cysteine, and
serine-valine-phenylalanine.

28. The method of claim 26, wherein said insertion peptide has 2 to 5 amino acid residues.

29. The method of claim 26, wherein said insertion peptide has 3 amino acid residues.

30. The method of claim 26, wherein said insertion peptide contains alanine residues at both ends thereof and has 3 to 6 residues.

31. The method of claim 26, wherein said insertion peptide contains as structural amino acid residues thereof, alanine and glycine, alanine and histidine, or alanine and arginine.

32. The method of claim 26, wherein said insertion peptide is selected from the group consisting of alanine-glycine-alanine, alanine-histidine-alanine, and alanine-arginine-alanine.

* * * * *

SEQUENCE LISTING

<160> NUMBER OF SEQ ID NOS: 9

<210> SEQ ID NO 1
<211> LENGTH: 2475
<212> TYPE: DNA
<213> ORGANISM: Bacillus sp. KSM-S237
<220> FEATURE:
<221> NAME/KEY: CDS
<222> LOCATION: (1)..(2475)

<400> SEQUENCE: 1

```
atg atg tta aga aag aaa aca aag cag ttg att tct tcc att ctt att       48
Met Met Leu Arg Lys Lys Thr Lys Gln Leu Ile Ser Ser Ile Leu Ile
1               5                   10                  15 tta gtt tta ctt cta tct tta ttt ccg gca gct ctt gca gca gaa gga       96
Leu Val Leu Leu Leu Ser Leu Phe Pro Ala Ala Leu Ala Ala Glu Gly
            20                  25                  30 aac act cgt gaa gac aat ttt aaa cat tta tta ggt aat gac aat gtt      144
Asn Thr Arg Glu Asp Asn Phe Lys His Leu Leu Gly Asn Asp Asn Val
        35                  40                  45 aaa cgc cct tct gag gct ggc gca tta caa tta caa gaa gtc gat gga      192
Lys Arg Pro Ser Glu Ala Gly Ala Leu Gln Leu Gln Glu Val Asp Gly
    50                  55                  60 caa atg aca tta gta gat caa cat gga gaa aaa att caa tta cgt gga      240
Gln Met Thr Leu Val Asp Gln His Gly Glu Lys Ile Gln Leu Arg Gly
65                  70                  75                  80 atg agt aca cac gga tta cag tgg ttt cct gag atc ttg aat gat aac      288
Met Ser Thr His Gly Leu Gln Trp Phe Pro Glu Ile Leu Asn Asp Asn
            85                  90                  95 gca tac aaa gct ctt tct aac gat tgg gat tcc aat atg att cgt ctt      336
Ala Tyr Lys Ala Leu Ser Asn Asp Trp Asp Ser Asn Met Ile Arg Leu
        100                 105                 110 gct atg tat gta ggt gaa aat ggg tac gct aca aac cct gag tta atc      384
Ala Met Tyr Val Gly Glu Asn Gly Tyr Ala Thr Asn Pro Glu Leu Ile
    115                 120                 125 aaa caa aga gtg att gat gga att gag tta gcg att gaa aat gac atg      432
Lys Gln Arg Val Ile Asp Gly Ile Glu Leu Ala Ile Glu Asn Asp Met
130                 135                 140 tat gtt att gtt gac tgg cat gtt cat gcg cca ggt gat cct aga gat      480
Tyr Val Ile Val Asp Trp His Val His Ala Pro Gly Asp Pro Arg Asp
145                 150                 155                 160 cct gtt tat gca ggt gct aaa gat ttc ttt aga gaa att gca gct tta      528
Pro Val Tyr Ala Gly Ala Lys Asp Phe Phe Arg Glu Ile Ala Ala Leu
            165                 170                 175 tac cct aat aat cca cac att att tat gag tta gcg aat gag ccg agt      576
Tyr Pro Asn Asn Pro His Ile Ile Tyr Glu Leu Ala Asn Glu Pro Ser
        180                 185                 190 agt aat aat aat ggt gga gca ggg att ccg aat aac gaa gaa ggt tgg      624
Ser Asn Asn Asn Gly Gly Ala Gly Ile Pro Asn Asn Glu Glu Gly Trp
    195                 200                 205
```

-continued

| | | |
|---|---|---|
| aaa gcg gta aaa gaa tat gct gat cca att gta gaa atg tta cgt aaa<br>Lys Ala Val Lys Glu Tyr Ala Asp Pro Ile Val Glu Met Leu Arg Lys<br>210                         215                      220 | 672 |
| agc ggt aat gca gat gac aac att atc att gtt ggt agt cca aac tgg<br>Ser Gly Asn Ala Asp Asp Asn Ile Ile Ile Val Gly Ser Pro Asn Trp<br>225                       230                      235                  240 | 720 |
| agt cag cgt ccg gac tta gca gct gat aat cca att gat gat cac cat<br>Ser Gln Arg Pro Asp Leu Ala Ala Asp Asn Pro Ile Asp Asp His His<br>                      245                      250                      255 | 768 |
| aca atg tat act gtt cac ttc tac act ggt tca cat gct gct tca act<br>Thr Met Tyr Thr Val His Phe Tyr Thr Gly Ser His Ala Ala Ser Thr<br>              260                      265                      270 | 816 |
| gaa agc tat ccg tct gaa act cct aac tct gaa aga gga aac gta atg<br>Glu Ser Tyr Pro Ser Glu Thr Pro Asn Ser Glu Arg Gly Asn Val Met<br>     275                      280                      285 | 864 |
| agt aac act cgt tat gcg tta gaa aac gga gta gcg gta ttt gca aca<br>Ser Asn Thr Arg Tyr Ala Leu Glu Asn Gly Val Ala Val Phe Ala Thr<br>290                         295                      300 | 912 |
| gag tgg gga acg agt caa gct agt gga gac ggt ggt cct tac ttt gat<br>Glu Trp Gly Thr Ser Gln Ala Ser Gly Asp Gly Gly Pro Tyr Phe Asp<br>305                         310                      315                  320 | 960 |
| gaa gca gat gta tgg att gaa ttt tta aat gaa aac aac att agc tgg<br>Glu Ala Asp Val Trp Ile Glu Phe Leu Asn Glu Asn Asn Ile Ser Trp<br>                      325                      330                      335 | 1008 |
| gct aac tgg tct tta acg aat aaa aat gaa gta tct ggt gca ttt aca<br>Ala Asn Trp Ser Leu Thr Asn Lys Asn Glu Val Ser Gly Ala Phe Thr<br>              340                      345                      350 | 1056 |
| cca ttc gag tta ggt aag tct aac gca acc aat ctt gac cca ggt cca<br>Pro Phe Glu Leu Gly Lys Ser Asn Ala Thr Asn Leu Asp Pro Gly Pro<br>           355                      360                      365 | 1104 |
| gat cat gtg tgg gca cca gaa gaa tta agt ctt tct gga gaa tat gta<br>Asp His Val Trp Ala Pro Glu Glu Leu Ser Leu Ser Gly Glu Tyr Val<br>370                         375                      380 | 1152 |
| cgt gct cgt att aaa ggt gtg aac tat gag cca atc gac cgt aca aaa<br>Arg Ala Arg Ile Lys Gly Val Asn Tyr Glu Pro Ile Asp Arg Thr Lys<br>385                         390                      395                  400 | 1200 |
| tac acg aaa gta ctt tgg gac ttt aat gat gga acg aag caa gga ttt<br>Tyr Thr Lys Val Leu Trp Asp Phe Asn Asp Gly Thr Lys Gln Gly Phe<br>                      405                      410                      415 | 1248 |
| gga gtg aat tcg gat tct cca aat aaa gaa ctt att gca gtt gat aat<br>Gly Val Asn Ser Asp Ser Pro Asn Lys Glu Leu Ile Ala Val Asp Asn<br>              420                      425                      430 | 1296 |
| gaa aac aac act ttg aaa gtt tcg gga tta gat gta agt aac gat gtt<br>Glu Asn Asn Thr Leu Lys Val Ser Gly Leu Asp Val Ser Asn Asp Val<br>           435                      440                      445 | 1344 |
| tca gat ggc aac ttc tgg gct aat gct cgt ctt tct gcc aac ggt tgg<br>Ser Asp Gly Asn Phe Trp Ala Asn Ala Arg Leu Ser Ala Asn Gly Trp<br>450                         455                      460 | 1392 |
| gga aaa agt gtt gat att tta ggt gct gag aag ctt aca atg gat gtt<br>Gly Lys Ser Val Asp Ile Leu Gly Ala Glu Lys Leu Thr Met Asp Val<br>465                         470                      475                  480 | 1440 |
| att gtt gat gaa cca acg acg gta gct att gcg gcg att cca caa agt<br>Ile Val Asp Glu Pro Thr Thr Val Ala Ile Ala Ala Ile Pro Gln Ser<br>                      485                      490                      495 | 1488 |
| agt aaa agt gga tgg gca aat cca gag cgt gct gtt cga gtg aac gcg<br>Ser Lys Ser Gly Trp Ala Asn Pro Glu Arg Ala Val Arg Val Asn Ala<br>                      500                      505                      510 | 1536 |
| gaa gat ttt gtc cag caa acg gac ggt aag tat aaa gct gga tta aca<br>Glu Asp Phe Val Gln Gln Thr Asp Gly Lys Tyr Lys Ala Gly Leu Thr | 1584 |

-continued

```
                515                 520                 525
att aca gga gaa gat gct cct aac cta aaa aat atc gct ttt cat gaa      1632
Ile Thr Gly Glu Asp Ala Pro Asn Leu Lys Asn Ile Ala Phe His Glu
530                 535                 540 gaa gat aac aat atg aac aac atc att ctg ttc gtg gga act gat gca      1680
Glu Asp Asn Asn Met Asn Asn Ile Ile Leu Phe Val Gly Thr Asp Ala
545                 550                 555                 560 gct gac gtt att tac tta gat aac att aaa gta att gga aca gaa gtt      1728
Ala Asp Val Ile Tyr Leu Asp Asn Ile Lys Val Ile Gly Thr Glu Val
                565                 570                 575 gaa att cca gtt gtt cat gat cca aaa gga gaa gct gtt ctt cct tct      1776
Glu Ile Pro Val Val His Asp Pro Lys Gly Glu Ala Val Leu Pro Ser
            580                 585                 590 gtt ttt gaa gac ggt aca cgt caa ggt tgg gac tgg gct gga gag tct      1824
Val Phe Glu Asp Gly Thr Arg Gln Gly Trp Asp Trp Ala Gly Glu Ser
        595                 600                 605 ggt gtg aaa aca gct tta aca att gaa gaa gca aac ggt tct aac gcg      1872
Gly Val Lys Thr Ala Leu Thr Ile Glu Glu Ala Asn Gly Ser Asn Ala
    610                 615                 620 tta tca tgg gaa ttt gga tat cca gaa gta aaa cct agt gat aac tgg      1920
Leu Ser Trp Glu Phe Gly Tyr Pro Glu Val Lys Pro Ser Asp Asn Trp
625                 630                 635                 640 gca aca gct cca cgt tta gat ttc tgg aaa tct gac ttg gtt cgc ggt      1968
Ala Thr Ala Pro Arg Leu Asp Phe Trp Lys Ser Asp Leu Val Arg Gly
                645                 650                 655 gag aat gat tat gta gct ttt gat ttc tat cta gat cca gtt cgt gca      2016
Glu Asn Asp Tyr Val Ala Phe Asp Phe Tyr Leu Asp Pro Val Arg Ala
            660                 665                 670 aca gaa ggc gca atg aat atc aat tta gta ttc cag cca cct act aac      2064
Thr Glu Gly Ala Met Asn Ile Asn Leu Val Phe Gln Pro Pro Thr Asn
        675                 680                 685 ggg tat tgg gta caa gca cca aaa acg tat acg att aac ttt gat gaa      2112
Gly Tyr Trp Val Gln Ala Pro Lys Thr Tyr Thr Ile Asn Phe Asp Glu
    690                 695                 700 tta gag gaa gcg aat caa gta aat ggt tta tat cac tat gaa gtg aaa      2160
Leu Glu Glu Ala Asn Gln Val Asn Gly Leu Tyr His Tyr Glu Val Lys
705                 710                 715                 720 att aac gta aga gat att aca aac att caa gat gac acg tta cta cgt      2208
Ile Asn Val Arg Asp Ile Thr Asn Ile Gln Asp Asp Thr Leu Leu Arg
                725                 730                 735 aac atg atg atc att ttt gca gat gta gaa agt gac ttt gca ggg aga      2256
Asn Met Met Ile Ile Phe Ala Asp Val Glu Ser Asp Phe Ala Gly Arg
            740                 745                 750 gtc ttt gta gat aat gtt cgt ttt gag ggg gct gct act act gag ccg      2304
Val Phe Val Asp Asn Val Arg Phe Glu Gly Ala Ala Thr Thr Glu Pro
        755                 760                 765 gtt gaa cca gag cca gtt gat cct ggc gaa gag acg cca cct gtc gat      2352
Val Glu Pro Glu Pro Val Asp Pro Gly Glu Glu Thr Pro Pro Val Asp
    770                 775                 780 gag aag gaa gcg aaa aaa gaa caa aaa gaa gca gag aaa gaa gag aaa      2400
Glu Lys Glu Ala Lys Lys Glu Gln Lys Glu Ala Glu Lys Glu Glu Lys
785                 790                 795                 800 gaa gca gta aaa gaa gaa aag aaa gaa gct aaa gaa gaa aag aaa gca      2448
Glu Ala Val Lys Glu Glu Lys Lys Glu Ala Lys Glu Glu Lys Lys Ala
                805                 810                 815 gtc aaa aat gag gct aag aaa aaa taa                                  2475
Val Lys Asn Glu Ala Lys Lys Lys
            820
```

-continued

<210> SEQ ID NO 2
<211> LENGTH: 824
<212> TYPE: PRT
<213> ORGANISM: Bacillus sp. KSM-S237

<400> SEQUENCE: 2

```
Met Met Leu Arg Lys Lys Thr Lys Gln Leu Ile Ser Ser Ile Leu Ile
1               5                   10                  15
Leu Val Leu Leu Leu Ser Leu Phe Pro Ala Ala Leu Ala Ala Glu Gly
            20                  25                  30
Asn Thr Arg Glu Asp Asn Phe Lys His Leu Leu Gly Asn Asp Asn Val
        35                  40                  45
Lys Arg Pro Ser Glu Ala Gly Ala Leu Gln Leu Gln Glu Val Asp Gly
    50                  55                  60
Gln Met Thr Leu Val Asp Gln His Gly Glu Lys Ile Gln Leu Arg Gly
65                  70                  75                  80
Met Ser Thr His Gly Leu Gln Trp Phe Pro Glu Ile Leu Asn Asp Asn
                85                  90                  95
Ala Tyr Lys Ala Leu Ser Asn Asp Trp Asp Ser Asn Met Ile Arg Leu
            100                 105                 110
Ala Met Tyr Val Gly Glu Asn Gly Tyr Ala Thr Asn Pro Glu Leu Ile
        115                 120                 125
Lys Gln Arg Val Ile Asp Gly Ile Glu Leu Ala Ile Glu Asn Asp Met
    130                 135                 140
Tyr Val Ile Val Asp Trp His Val His Ala Pro Gly Asp Pro Arg Asp
145                 150                 155                 160
Pro Val Tyr Ala Gly Ala Lys Asp Phe Phe Arg Glu Ile Ala Ala Leu
                165                 170                 175
Tyr Pro Asn Asn Pro His Ile Ile Tyr Glu Leu Ala Asn Glu Pro Ser
            180                 185                 190
Ser Asn Asn Asn Gly Gly Ala Gly Ile Pro Asn Asn Glu Glu Gly Trp
        195                 200                 205
Lys Ala Val Lys Glu Tyr Ala Asp Pro Ile Val Glu Met Leu Arg Lys
    210                 215                 220
Ser Gly Asn Ala Asp Asp Asn Ile Ile Ile Val Gly Ser Pro Asn Trp
225                 230                 235                 240
Ser Gln Arg Pro Asp Leu Ala Ala Asp Asn Pro Ile Asp Asp His His
                245                 250                 255
Thr Met Tyr Thr Val His Phe Tyr Thr Gly Ser His Ala Ala Ser Thr
            260                 265                 270
Glu Ser Tyr Pro Ser Glu Thr Pro Asn Ser Glu Arg Gly Asn Val Met
        275                 280                 285
Ser Asn Thr Arg Tyr Ala Leu Glu Asn Gly Val Ala Val Phe Ala Thr
    290                 295                 300
Glu Trp Gly Thr Ser Gln Ala Ser Gly Asp Gly Gly Pro Tyr Phe Asp
305                 310                 315                 320
Glu Ala Asp Val Trp Ile Glu Phe Leu Asn Glu Asn Asn Ile Ser Trp
                325                 330                 335
Ala Asn Trp Ser Leu Thr Asn Lys Asn Glu Val Ser Gly Ala Phe Thr
            340                 345                 350
Pro Phe Glu Leu Gly Lys Ser Asn Ala Thr Asn Leu Asp Pro Gly Pro
        355                 360                 365
Asp His Val Trp Ala Pro Glu Glu Leu Ser Leu Ser Gly Glu Tyr Val
    370                 375                 380
```

-continued

```
Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
            420                 425                 430

Glu Asn Asn Thr Leu Lys Val Ser Gly Leu Asp Val Ser Asn Asp Val
        435                 440                 445

Ser Asp Gly Asn Phe Trp Ala Asn Ala Arg Leu Ser Ala Asn Gly Trp
    450                 455                 460

Gly Lys Ser Val Asp Ile Leu Gly Ala Glu Lys Leu Thr Met Asp Val
465                 470                 475                 480

Ile Val Asp Glu Pro Thr Thr Val Ala Ile Ala Ala Ile Pro Gln Ser
                485                 490                 495

Ser Lys Ser Gly Trp Ala Asn Pro Glu Arg Ala Val Arg Val Asn Ala
            500                 505                 510

Glu Asp Phe Val Gln Gln Thr Asp Gly Lys Tyr Lys Ala Gly Leu Thr
        515                 520                 525

Ile Thr Gly Glu Asp Ala Pro Asn Leu Lys Asn Ile Ala Phe His Glu
    530                 535                 540

Glu Asp Asn Asn Met Asn Asn Ile Ile Leu Phe Val Gly Thr Asp Ala
545                 550                 555                 560

Ala Asp Val Ile Tyr Leu Asp Asn Ile Lys Val Ile Gly Thr Glu Val
                565                 570                 575

Glu Ile Pro Val Val His Asp Pro Lys Gly Glu Ala Val Leu Pro Ser
            580                 585                 590

Val Phe Glu Asp Gly Thr Arg Gln Gly Trp Asp Trp Ala Gly Glu Ser
        595                 600                 605

Gly Val Lys Thr Ala Leu Thr Ile Glu Glu Ala Asn Gly Ser Asn Ala
    610                 615                 620

Leu Ser Trp Glu Phe Gly Tyr Pro Glu Val Lys Pro Ser Asp Asn Trp
625                 630                 635                 640

Ala Thr Ala Pro Arg Leu Asp Phe Trp Lys Ser Asp Leu Val Arg Gly
                645                 650                 655

Glu Asn Asp Tyr Val Ala Phe Asp Phe Tyr Leu Asp Pro Val Arg Ala
            660                 665                 670

Thr Glu Gly Ala Met Asn Ile Asn Leu Val Phe Gln Pro Pro Thr Asn
        675                 680                 685

Gly Tyr Trp Val Gln Ala Pro Lys Thr Tyr Thr Ile Asn Phe Asp Glu
    690                 695                 700

Leu Glu Glu Ala Asn Gln Val Asn Gly Leu Tyr His Tyr Glu Val Lys
705                 710                 715                 720

Ile Asn Val Arg Asp Ile Thr Asn Ile Gln Asp Asp Thr Leu Leu Arg
                725                 730                 735

Asn Met Met Ile Ile Phe Ala Asp Val Glu Ser Asp Phe Ala Gly Arg
            740                 745                 750

Val Phe Val Asp Asn Val Arg Phe Glu Gly Ala Ala Thr Thr Glu Pro
        755                 760                 765

Val Glu Pro Glu Pro Val Asp Pro Gly Glu Glu Thr Pro Pro Val Asp
    770                 775                 780

Glu Lys Glu Ala Lys Lys Glu Gln Lys Glu Ala Glu Lys Glu Glu Lys
785                 790                 795                 800

Glu Ala Val Lys Glu Glu Lys Lys Glu Ala Lys Glu Glu Lys Lys Ala
```

|              | 805           | 810          | 815       |
|--------------|---------------|--------------|-----------|

Val Lys Asn Glu Ala Lys Lys Lys
            820

<210> SEQ ID NO 3
<211> LENGTH: 54
<212> TYPE: DNA
<213> ORGANISM: Artificial Sequence
<220> FEATURE:
<223> OTHER INFORMATION: Synthetic DNA

<400> SEQUENCE: 3
gtgcatttac accattcgag ttagctggcg caaatcttga cccaggtcca gatc        54

<210> SEQ ID NO 4
<211> LENGTH: 34
<212> TYPE: DNA
<213> ORGANISM: Artificial Sequence
<220> FEATURE:
<223> OTHER INFORMATION: Synthetic DNA

<400> SEQUENCE: 4
ccattcgagt tagctcacgc aaatcttgac ccag        34

<210> SEQ ID NO 5
<211> LENGTH: 34
<212> TYPE: DNA
<213> ORGANISM: Artificial Sequence
<220> FEATURE:
<223> OTHER INFORMATION: Synthetic DNA

<400> SEQUENCE: 5
ccattcgagt tagctcgtgc aaatcttgac ccag        34

<210> SEQ ID NO 6
<211> LENGTH: 31
<212> TYPE: DNA
<213> ORGANISM: Artificial Sequence
<220> FEATURE:
<223> OTHER INFORMATION: Synthetic DNA

<400> SEQUENCE: 6
caataacatc cattgtaagc ttctcagcac c        31

<210> SEQ ID NO 7
<211> LENGTH: 800
<212> TYPE: PRT
<213> ORGANISM: Bacillus sp. strain 1139

<400> SEQUENCE: 7

Met Met Leu Arg Lys Lys Thr Lys Gln Leu Ile Ser Ser Ile Leu Ile
1               5                   10                  15

Leu Val Leu Leu Leu Ser Leu Phe Pro Thr Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

-continued

```
Ala Tyr Lys Ala Leu Ala Asn Asp Trp Glu Ser Asn Met Ile Arg Leu
            100                 105                 110
Ala Met Tyr Val Gly Glu Asn Gly Tyr Ala Ser Asn Pro Glu Leu Ile
        115                 120                 125
Lys Ser Arg Val Ile Lys Gly Ile Asp Leu Ala Ile Glu Asn Asp Met
    130                 135                 140
Tyr Val Ile Val Asp Trp His Val His Ala Pro Gly Asp Pro Arg Asp
145                 150                 155                 160
Pro Val Tyr Ala Gly Ala Glu Asp Phe Phe Arg Asp Ile Ala Ala Leu
                165                 170                 175
Tyr Pro Asn Asn Pro His Ile Ile Tyr Glu Leu Ala Asn Glu Pro Ser
            180                 185                 190
Ser Asn Asn Asn Gly Gly Ala Gly Ile Pro Asn Asn Glu Glu Gly Trp
        195                 200                 205
Asn Ala Val Lys Glu Tyr Ala Asp Pro Ile Val Glu Met Leu Arg Asp
    210                 215                 220
Ser Gly Asn Ala Asp Asp Asn Ile Ile Ile Val Gly Ser Pro Asn Trp
225                 230                 235                 240
Ser Gln Arg Pro Asp Leu Ala Ala Asp Asn Pro Ile Asp Asp His His
                245                 250                 255
Thr Met Tyr Thr Val His Phe Tyr Thr Gly Ser His Ala Ala Ser Thr
            260                 265                 270
Glu Ser Tyr Pro Pro Glu Thr Pro Asn Ser Glu Arg Gly Asn Val Met
        275                 280                 285
Ser Asn Thr Arg Tyr Ala Leu Glu Asn Gly Val Ala Val Phe Ala Thr
    290                 295                 300
Glu Trp Gly Thr Ser Gln Ala Asn Gly Asp Gly Gly Pro Tyr Phe Asp
305                 310                 315                 320
Glu Ala Asp Val Trp Ile Glu Phe Leu Asn Glu Asn Asn Ile Ser Trp
                325                 330                 335
Ala Asn Trp Ser Leu Thr Asn Lys Asn Glu Val Ser Gly Ala Phe Thr
            340                 345                 350
Pro Phe Glu Leu Gly Lys Ser Asn Ala Thr Ser Leu Asp Pro Gly Pro
        355                 360                 365
Asp Gln Val Trp Val Pro Glu Glu Leu Ser Leu Ser Gly Glu Tyr Val
    370                 375                 380
Arg Ala Arg Ile Lys Gly Val Asn Tyr Glu Pro Ile Asp Arg Thr Lys
385                 390                 395                 400
Tyr Thr Lys Val Leu Trp Asp Phe Asn Asp Gly Thr Lys Gln Gly Phe
                405                 410                 415
Gly Val Asn Gly Asp Ser Pro Val Glu Asp Val Val Ile Glu Asn Glu
            420                 425                 430
Ala Gly Ala Leu Lys Leu Ser Gly Leu Asp Ala Ser Asn Asp Val Ser
        435                 440                 445
Glu Gly Asn Tyr Trp Ala Asn Ala Arg Leu Ser Ala Asp Gly Trp Gly
    450                 455                 460
Lys Ser Val Asp Ile Leu Gly Ala Glu Lys Leu Thr Met Asp Val Ile
465                 470                 475                 480
Val Asp Glu Pro Thr Thr Val Ser Ile Ala Ile Pro Gln Gly Pro
                485                 490                 495
Ser Ala Asn Trp Val Asn Pro Asn Arg Ala Ile Lys Val Glu Pro Thr
            500                 505                 510
Asn Phe Val Pro Leu Glu Asp Lys Phe Lys Ala Glu Leu Thr Ile Thr
```

-continued

```
                515                 520                 525
Ser Ala Asp Ser Pro Ser Leu Glu Ala Ile Ala Met His Ala Glu Asn
        530                 535                 540

Asn Asn Ile Asn Asn Ile Ile Leu Phe Val Gly Thr Glu Gly Ala Asp
545                 550                 555                 560

Val Ile Tyr Leu Asp Asn Ile Lys Val Ile Gly Thr Glu Val Glu Ile
                565                 570                 575

Pro Val Val His Asp Pro Lys Gly Glu Ala Val Leu Pro Ser Val Phe
            580                 585                 590

Glu Asp Gly Thr Arg Gln Gly Trp Asp Trp Ala Gly Ser Gly Val
        595                 600                 605

Lys Thr Ala Leu Thr Ile Glu Glu Ala Asn Gly Ser Asn Ala Leu Ser
        610                 615                 620

Trp Glu Phe Gly Tyr Pro Glu Val Lys Pro Ser Asp Asn Trp Ala Thr
625                 630                 635                 640

Ala Pro Arg Leu Asp Phe Trp Lys Ser Asp Leu Val Arg Gly Glu Asn
                645                 650                 655

Asp Tyr Val Thr Phe Asp Phe Tyr Leu Asp Pro Val Arg Ala Thr Glu
                660                 665                 670

Gly Ala Met Asn Ile Asn Leu Val Phe Gln Pro Pro Thr Asn Gly Tyr
        675                 680                 685

Trp Val Gln Ala Pro Lys Thr Tyr Thr Ile Asn Phe Asp Glu Leu Glu
        690                 695                 700

Glu Pro Asn Gln Val Asn Gly Leu Tyr His Tyr Glu Val Lys Ile Asn
705                 710                 715                 720

Val Arg Asp Ile Thr Asn Ile Gln Asp Asp Thr Leu Leu Arg Asn Met
                725                 730                 735

Met Ile Ile Phe Ala Asp Val Glu Ser Asp Phe Ala Gly Arg Val Phe
                740                 745                 750

Val Asp Asn Val Arg Phe Glu Gly Ala Ala Thr Thr Glu Pro Val Glu
            755                 760                 765

Pro Glu Pro Val Asp Pro Gly Glu Glu Thr Pro Val Asp Glu Lys
        770                 775                 780

Glu Ala Lys Thr Glu Gln Lys Glu Ala Glu Lys Glu Glu Lys Glu Glu
785                 790                 795                 800
```

<210> SEQ ID NO 8
<211> LENGTH: 822
<212> TYPE: PRT
<213> ORGANISM: Bacillus sp. strain KSM-64

<400> SEQUENCE: 8

```
Met Met Leu Arg Lys Lys Thr Lys Gln Leu Ile Ser Ser Ile Leu Ile
1               5                   10                  15

Leu Val Leu Leu Leu Ser Leu Phe Pro Thr Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95
```

```
Ala Tyr Lys Ala Leu Ala Asn Asp Trp Glu Ser Asn Met Ile Arg Leu
                100                 105                 110

Ala Met Tyr Val Gly Glu Asn Gly Tyr Ala Ser Asn Pro Glu Leu Ile
            115                 120                 125

Lys Ser Arg Val Ile Lys Gly Ile Asp Leu Ala Ile Glu Asn Asp Met
        130                 135                 140

Tyr Val Ile Val Asp Trp His Val His Ala Pro Gly Asp Pro Arg Asp
145                 150                 155                 160

Pro Val Tyr Ala Gly Ala Glu Asp Phe Phe Arg Asp Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
        195                 200                 205

Asn Ala Val Lys Glu Tyr Ala Asp Pro Ile Val Glu Met Leu Arg Asp
        210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Pro Glu Thr Pro Asn Ser Glu Arg Gly Asn Val Met
        275                 280                 285

Ser Asn Thr Arg Tyr Ala Leu Glu Asn Gly Val Ala Val Phe Ala Thr
        290                 295                 300

Glu Trp Gly Thr Ser Gln Ala Asn Gly Asp Gly Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Ser Leu Asp Pro Gly Pro
        355                 360                 365

Asp Gln Val Trp Val Pro Glu Glu Leu Ser Leu Ser Gly Glu Tyr Val
        370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Gly Asp Ser Pro Val Glu Asp Val Val Ile Glu Asn Glu
            420                 425                 430

Ala Gly Ala Leu Lys Leu Ser Gly Leu Asp Ala Ser Asn Asp Val Ser
        435                 440                 445

Glu Gly Asn Tyr Trp Ala Asn Ala Arg Leu Ser Ala Asp Gly Trp Gly
        450                 455                 460

Lys Ser Val Asp Ile Leu Gly Ala Glu Lys Leu Thr Met Asp Val Ile
465                 470                 475                 480

Val Asp Glu Pro Thr Thr Val Ser Ile Ala Ala Ile Pro Gln Gly Pro
                485                 490                 495

Ser Ala Asn Trp Val Asn Pro Asn Arg Ala Ile Lys Val Glu Pro Thr
            500                 505                 510

Asn Phe Val Pro Leu Gly Asp Lys Phe Lys Ala Glu Leu Thr Ile Thr
```

-continued

```
                515                 520                 525

Ser Ala Asp Ser Pro Ser Leu Glu Ala Ile Ala Met His Ala Glu Asn
        530                 535                 540

Asn Asn Ile Asn Asn Ile Ile Leu Phe Val Gly Thr Glu Gly Ala Asp
545                 550                 555                 560

Val Ile Tyr Leu Asp Asn Ile Lys Val Ile Gly Thr Glu Val Glu Ile
                565                 570                 575

Pro Val Val His Asp Pro Lys Gly Glu Ala Val Leu Pro Ser Val Phe
            580                 585                 590

Glu Asp Gly Thr Arg Gln Gly Trp Asp Trp Ala Gly Glu Ser Gly Val
        595                 600                 605

Lys Thr Ala Leu Thr Ile Glu Glu Ala Asn Gly Ser Asn Ala Leu Ser
    610                 615                 620

Trp Glu Phe Gly Tyr Pro Glu Val Lys Pro Ser Asp Asn Trp Ala Thr
625                 630                 635                 640

Ala Pro Arg Leu Asp Phe Trp Lys Ser Asp Leu Val Arg Gly Glu Asn
                645                 650                 655

Asp Tyr Val Thr Phe Asp Phe Tyr Leu Asp Pro Val Arg Ala Thr Glu
            660                 665                 670

Gly Ala Met Asn Ile Asn Leu Val Phe Gln Pro Pro Thr Asn Gly Tyr
        675                 680                 685

Trp Val Gln Ala Pro Lys Thr Tyr Thr Ile Asn Phe Asp Glu Leu Glu
    690                 695                 700

Glu Ala Asn Gln Val Asn Gly Leu Tyr His Tyr Glu Val Lys Ile Asn
705                 710                 715                 720

Val Arg Asp Ile Thr Asn Ile Gln Asp Asp Thr Leu Leu Arg Asn Met
                725                 730                 735

Met Ile Ile Phe Ala Asp Val Glu Ser Asp Phe Ala Gly Arg Val Phe
            740                 745                 750

Val Asp Asn Val Arg Phe Glu Gly Ala Ala Thr Thr Glu Pro Val Glu
        755                 760                 765

Pro Glu Pro Val Asp Pro Gly Glu Glu Thr Pro Pro Val Asp Glu Lys
    770                 775                 780

Glu Ala Lys Lys Glu Gln Lys Glu Ala Glu Lys Glu Lys Glu Lys Ala
785                 790                 795                 800

Val Lys Glu Glu Lys Lys Glu Ala Lys Glu Glu Lys Lys Ala Ile Lys
                805                 810                 815

Asn Glu Ala Thr Lys Lys
            820

<210> SEQ ID NO 9
<211> LENGTH: 810
<212> TYPE: PRT
<213> ORGANISM: Bacillus sp. strain KSM-N131

<400> SEQUENCE: 9

Met Met Leu Arg Lys Lys Thr Lys Gln Leu Gly Arg Pro Ala Gln Ala
1               5                   10                  15

Glu Gly Asn Thr Arg Glu Asp Asn Phe Lys His Leu Leu Gly Asn Asp
            20                  25                  30

Asn Val Lys Arg Pro Ser Glu Ala Gly Ala Leu Gln Leu Gln Glu Val
        35                  40                  45

Asp Gly Gln Met Thr Leu Val Asp Gln His Gly Glu Lys Ile Gln Leu
    50                  55                  60
```

```
Arg Gly Met Ser Thr His Gly Leu Gln Trp Phe Pro Glu Ile Leu Asn
 65                  70                  75                  80

Asp Asn Ala Tyr Lys Ala Leu Ser Asn Asp Trp Asp Ser Asn Met Ile
                 85                  90                  95

Arg Leu Ala Met Tyr Val Gly Glu Asn Gly His Ala Thr Asn Pro Glu
            100                 105                 110

Leu Ile Lys Gln Arg Val Ile Asp Gly Ile Glu Leu Ala Ile Glu Asn
        115                 120                 125

Asp Met Tyr Val Ile Val Asp Trp His Val His Ala Pro Gly Asp Pro
    130                 135                 140

Arg Asp Pro Val Tyr Ala Gly Ala Lys Asp Phe Phe Arg Glu Ile Ala
145                 150                 155                 160

Ala Leu Tyr Pro Asn Asn Pro His Ile Ile Tyr Glu Leu Ala Asn Glu
                165                 170                 175

Pro Ser Ser Asn Asn Asn Gly Gly Ala Gly Ile Pro Asn Asn Glu Glu
                180                 185                 190

Gly Trp Lys Ala Val Lys Glu Tyr Ala Asp Pro Ile Val Gln Met Leu
            195                 200                 205

Arg Lys Ser Gly Asn Ala Asp Asp Asn Ile Ile Val Gly Ser Pro
        210                 215                 220

Asn Trp Ser Gln Arg Pro Asp Leu Ala Ala Asp Asn Pro Ile Asp Asp
225                 230                 235                 240

His His Thr Met Tyr Thr Val His Phe Tyr Thr Gly Ser His Ala Ala
                245                 250                 255

Ser Thr Glu Ser Tyr Pro Pro Glu Thr Pro Asn Ser Glu Arg Gly Asn
                260                 265                 270

Val Met Ser Asn Thr Arg Tyr Ala Leu Glu Asn Gly Val Ala Val Phe
            275                 280                 285

Ala Thr Glu Trp Gly Thr Ser Gln Ala Asn Gly Asp Gly Gly Pro Tyr
            290                 295                 300

Phe Asp Glu Ala Asp Val Trp Ile Glu Phe Leu Asn Glu Asn Asn Ile
305                 310                 315                 320

Ser Trp Ala Asn Trp Ser Leu Thr Asn Lys Asn Glu Val Ser Gly Ala
                325                 330                 335

Phe Thr Pro Phe Glu Leu Gly Lys Ser Asn Ala Thr Ser Leu Asp Pro
            340                 345                 350

Gly Pro Asp Gln Val Trp Val Pro Glu Glu Leu Ser Leu Ser Gly Glu
            355                 360                 365

Tyr Val Arg Ala Arg Ile Lys Gly Val Asn Tyr Glu Pro Ile Asp Arg
            370                 375                 380

Thr Lys Tyr Thr Lys Val Leu Trp Asp Phe Asn Asp Gly Thr Lys Gln
385                 390                 395                 400

Gly Phe Gly Val Asn Ser Asp Ser Pro Asn Lys Glu Leu Ile Ala Val
            405                 410                 415

Asp Asn Glu Asn Asn Thr Leu Lys Val Ser Gly Leu Asp Val Ser Asn
            420                 425                 430

Asp Val Ser Asp Gly Asn Phe Trp Ala Asn Ala Arg Leu Ser Ala Asn
        435                 440                 445

Gly Trp Gly Lys Ser Val Asp Ile Leu Gly Ala Glu Lys Leu Thr Met
    450                 455                 460

Asp Val Ile Val Asp Glu Pro Thr Thr Val Ala Ile Ala Ala Ile Pro
465                 470                 475                 480

Gln Ser Ser Lys Ser Gly Trp Ala Asn Pro Glu Arg Ala Val Arg Val
```

-continued

```
                    485                 490                 495
Asn Ala Glu Asp Phe Val Gln Gln Thr Asp Gly Lys Tyr Lys Ala Gly
            500                 505                 510
Leu Thr Ile Thr Gly Glu Asp Ala Pro Ser Leu Glu Ala Ile Ala Met
            515                 520                 525
His Ala Glu Asn Tyr Thr Ile Asn Asn Ile Ile Leu Phe Val Gly Thr
            530                 535                 540
Glu Gly Ala Asp Val Ile Tyr Leu Asp Thr Ile Lys Val Ile Gly Pro
545                     550                 555                 560
Glu Val Glu Ile Pro Val Val His Asp Pro Lys Gly Glu Ala Val Leu
            565                 570                 575
Pro Ser Val Phe Glu Asp Gly Thr Arg Gln Gly Trp Asp Trp Ala Gly
            580                 585                 590
Glu Ser Gly Val Lys Thr Ala Leu Thr Ile Glu Glu Ala Asn Gly Ser
            595                 600                 605
Asn Ala Leu Ser Trp Glu Phe Gly Tyr Pro Glu Val Lys Pro Ser Asp
            610                 615                 620
Asn Trp Ala Thr Ala Pro Arg Leu Asp Phe Trp Lys Ser Asp Leu Val
625                     630                 635                 640
Arg Gly Glu Asn Asp Tyr Val Thr Phe Asp Phe Tyr Leu Asp Pro Val
            645                 650                 655
Arg Ala Thr Glu Gly Ala Met Asn Ile Asn Leu Val Phe Gln Pro Pro
            660                 665                 670
Thr Asn Gly Tyr Trp Val Gln Ala Pro Lys Thr Tyr Thr Ile Asn Phe
            675                 680                 685
Asp Glu Leu Glu Glu Ala Asn Gln Val Asn Gly Leu Tyr His Tyr Glu
            690                 695                 700
Val Lys Ile Asn Val Arg Asp Ile Thr Asn Ile Gln Asp Asp Thr Leu
705                     710                 715                 720
Leu Arg Asn Met Met Ile Ile Phe Ala Asp Val Glu Ser Asp Phe Ala
            725                 730                 735
Gly Arg Val Phe Val Asp Asn Val Arg Phe Glu Gly Ala Ala Thr Thr
            740                 745                 750
Glu Pro Val Glu Pro Glu Pro Val Asp Pro Gly Glu Glu Thr Pro Pro
            755                 760                 765
Val Asp Glu Lys Glu Ala Lys Lys Glu Gln Lys Glu Ala Glu Lys Glu
            770                 775                 780
Glu Lys Glu Ala Val Lys Glu Glu Lys Lys Glu Ala Lys Glu Glu Lys
785                     790                 795                 800
Lys Ala Ile Lys Asn Glu Ala Thr Lys Lys
            805                 810
```